(12) United States Patent
Mitsui et al.

(10) Patent No.: US 7,749,213 B2
(45) Date of Patent: Jul. 6, 2010

(54) DISPOSABLE DIAPER

(75) Inventors: Koichiro Mitsui, Kagawa-ken (JP);
Yasushi Sayama, Kagawa-ken (JP);
Hironao Minato, Kagawa-ken (JP);
Koichiro Tani, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 600 days.

(21) Appl. No.: 10/673,260

(22) Filed: Sep. 30, 2003

(65) Prior Publication Data

US 2004/0073188 A1 Apr. 15, 2004

(30) Foreign Application Priority Data

Oct. 10, 2002 (JP) .............................. 2002-298089

(51) Int. Cl.
*A61F 13/15* (2006.01)
*A61F 13/20* (2006.01)

(52) U.S. Cl. ...................................... 604/391; 604/386

(58) Field of Classification Search ................. 604/391, 604/385.04, 386, 387, 393, 394, 402
See application file for complete search history.

(56) References Cited

U.S. PATENT DOCUMENTS

| 4,066,081 | A | * | 1/1978 | Schaar | 604/390 |
| 4,778,701 | A | * | 10/1988 | Pape et al. | 428/41.8 |
| 4,795,456 | A | * | 1/1989 | Borgers et al. | 604/390 |
| 5,057,097 | A | * | 10/1991 | Gesp | 604/389 |
| 6,730,069 | B2 | * | 5/2004 | Tanzer et al. | 604/391 |
| 2002/0138062 | A1 | * | 9/2002 | Kuen et al. | 604/386 |

FOREIGN PATENT DOCUMENTS

| CA | 2143791 A | * | 2/1996 |
| EP | 0 563 457 | | 10/1993 |
| EP | 0 755 665 | | 1/1997 |
| EP | 0 927 550 | | 7/1999 |
| EP | 0 974 326 | | 1/2000 |
| JP | 10-234779 A | | 9/1998 |
| JP | 11-276524 A | | 10/1999 |
| JP | 11276524 A | * | 10/1999 |
| JP | 2001-037806 A | | 2/2001 |

(Continued)

OTHER PUBLICATIONS

English translation of JP 2002-000648.*
English translation of JP 2002-000648 to Jingu et al.*

*Primary Examiner*—Melanie J Hand
(74) *Attorney, Agent, or Firm*—Lowe Hauptman Ham & Berner LLP

(57) ABSTRACT

In a disposable diaper includes a pair of side flaps respectively extending from an end portion in a lateral direction of the diaper main body and a fixing tape disposed in proximity of a farthest edge of the respective side flaps, the fixing tape is provided with a hook member, the fixing tape and the side flaps are to be engaged via the hook member, and an engaging region on the side flaps where the fixing tape is to be engaged includes portions having a different engaging force with the hook member. As a result, the fixing tape can be temporarily fixed with a modest engaging force, despite the hook member having a greater engaging force.

10 Claims, 8 Drawing Sheets

FOREIGN PATENT DOCUMENTS

| | | |
|---|---|---|
| JP | 2002-000648 A | 1/2002 |
| JP | 2002-45214 | 2/2002 |
| JP | 2002-253607 A | 9/2002 |
| WO | WO 97/28774 * | 8/1997 |
| WO | WO 9728774 A1 * | 8/1997 |
| WO | 00 27329 | 5/2000 |

* cited by examiner

DISPOSABLE DIAPER

FIELD OF THE INVENTION

The present invention relates to a tape-fixing type disposable diaper, more specifically to a disposable diaper provided with a pair of side flaps respectively having a fixing tape with a hook member.

BACKGROUND ART

A commercially available disposable diaper is comprised of a top sheet, a back sheet and an absorbent body disposed in a region that covers the crotch area of a wearer when he or she wears the diaper, and generally has a hourglass shape, i.e., a rectangular shape with a recess at a central portion of the longitudinal sides thereof. The recess corresponds to the crotch area of a wearer, and a wider portion extending from the recess of the crotch area comprises the dorsal section, while the opposite portion comprises the ventral section. A fixing tape is provided at a lateral edge of a wing piece extending from both sides of the dorsal section.

When using such a disposable diaper, the diaper is fitted onto a wearer in an ordinary manner and the fixing tape at the lateral edge of the wing piece of the dorsal section is attached to a wearer by fixing around the waist, which is at the opposite side of the disposable diaper. Among various types of the fixing tape, one with a hook member is more preferable because of the advantage that the fixing tape can be repeatedly joined and released.

The fixing tape is disposed so as to protrude outwardly from the lateral edge of the wing pieces of the disposable diaper, as described in the Japanese Patent Publication No. 2002-45214.

In a manufacturing process of the disposable diaper provided with fixing tape so as to extend outwardly at the lateral edge of each wing niece of the diaper main body, the disposable diaper proceeds with the assembling and folding steps, etc., while continuously moving along a manufacturing line. In this case, since the fixing tape is provided so as to protrude outwardly, the fixing tape may be caught in a machine or hooked with another part of the diaper, thereby interrupting the smooth flow of production. Further, an entire diaper may even get caught in a machine.

A remedy for preventing such a failure is to fold back the fixing tape toward a wing piece, for temporary fixation to a bulky nonwoven fabric at a surface of the diaper with the hook member of the fixing tape. Accordingly, since the fixing tape is no longer protruding outwardly from the lateral edge of the wing piece, the fixing tape can be prevented from getting caught in the machine or causing a similar failure.

However, in a case where the wing piece of the disposable diaper is comprised of an elastic side flap, the nonwoven fabric at the surface becomes bulkier because of the elasticity of the side flap. Therefore, when the fixing tape is temporarily fixed by the hook member, the hook member is tightly engaged with the bulky nonwoven fabric. As a result, it becomes difficult to separate the fixing tape temporarily fixed to the side flap surface when fitting the diaper onto a wearer, and the side flap surface is prone to damage.

Another solution is to apply an adhesive for temporary fixing to an area close to the hook member, and to temporarily fix the fixing tape with the adhesive for temporary fixing by folding back the fixing tape such that the hook member is disposed inside. However, such remedy requires an additional process of applying the adhesive for temporary fixing in advance prior to performing the temporary fixing, and resultantly the manufacturing process becomes more complicated. Moreover, the manufacturing cost is undesirably increased.

DISCLOSURE OF THE INVENTION

The present invention has been conceived in view of the foregoing drawbacks, with an object to provide a disposable diaper comprising a pair of side flaps respectively extending outwardly from the end portion in the lateral direction of the diaper main body, wherein a fixing tape having a hook member is disposed in proximity of a farthest lateral edge of the side flap such that the fixing tape can be temporarily fixed to the side flap.

For achieving the above object, the present invention provides a fixing tape comprising a hook member disposed on a surface of the tape substrate. This fixing tape is installed in such a manner that the hook member opposes the side flap surface, so that the fixing tape is engaged with the side flap surface through an engaging region comprised of an engaging portion and a non-engaging portion. It has been found that in this manner the fixing tape can be temporarily fixed to the side flap surface with an appropriate engaging force.

More specifically, the present invention provides the following.

(1) A disposable diaper comprising a diaper main body including a top sheet, a back sheet and an absorbent body enclosed in the sheets; a pair of side flaps respectively extending outwardly from an end portion in a lateral direction of the diaper main body; and a fixing tape disposed in proximity of a farthest lateral edge of the respective side flaps extending outwardly; wherein the fixing tape is provided with a hook member; the fixing tape and the side flap are to be engaged via the hook member; and an engaging region on the side flap where the fixing tape is to be engaged includes portions having a different engaging force with the hook member.

According to the present invention, in a disposable diaper comprising a fixing tape having a hook member attached to a side flap wherein engagement between the fixing tape and the side flap is achieved by engagement between the hook member and the side flap, an engaging region, i.e. a region where the fixing tape is to be engaged, includes portions having a different engaging force with the hook member. Therefore, the engaging force between the fixing tape and the side flap can be controlled by appropriately selecting the engaging region for engagement with the hook member. Consequently, a suitable engaging force that does not cause damage to the side flap in a case where the fixing tape is temporarily fixed to the side flap can be selected according to the material used as the side flap. For example, even in a case where a bulky elastic nonwoven fabric is used as the side flap for improving fitness of the diaper around the waist or legs of a wearer, the fixing tape temporarily fixed to the side flap can be separated with a small force. As a result, the side flap surface can be prevented from being damaged. On the other hand, when the diaper is applied to a wearer, since an entire surface of the hook member is engaged with the diaper surface a sufficient engaging force can be obtained, which retains the diaper in place.

Also, since the fixing tape is temporarily fixed to the side flap as described above, the fixing tape does not protrude outwardly from the lateral edge of the side flap of the diaper. Accordingly, in a manufacturing process of the diaper, when the diaper continuously moves along a manufacturing line to proceed with assembling and folding steps, etc., the fixing tape does not get caught in a machine or hooked with another part of the diaper, therefore a smooth flow of production can be maintained. Further, the possibility of a failure such that an entire diaper gets caught in a machine becomes minimal.

Here, the engaging region means a region on a mating region with which the hook member provided on the fixing tape is to be engaged. Likewise, the engaging portion means a portion with which the hook member is to be engaged. For example, in a case where the hook member provided on the fixing tape is a male engaging piece such as an engaging piece implanted with hook-shaped engaging elements or an engaging piece implanted with mushroom-shaped engaging elements, a female engaging piece such as a loop-type engaging piece or bulky nonwoven fabric can be employed as an engaging portion. Further, the engaging force is represented by resistance against a force applied to separate the engaged portions. The engaging force can also be referred to as engaging strength.

(2) The disposable diaper according to (1), wherein the engaging region comprises an engaging portion with which the hook member is to be engaged and a non-engaging portion with which the hook member can barely be engaged or cannot be engaged at all.

According to the present invention, the engaging region comprises an engaging portion with which the hook member is to be engaged and a non-engaging portion with which the hook member can barely be engaged or cannot be engaged at all. Therefore, when the hook member is engaged with an engaging region, the engaging force between the side flap and the fixing tape depends on an engaging force at an engaging portion with which the hook member is engaged. Accordingly the engaging force can be controlled as desired by adjusting an area of the engaging portion. Specifically, the larger the engaging portion is the greater the engaging force becomes, but the engaging force becomes smaller as the engaging portion is reduced. As a result, it becomes possible to separate the fixing tape with a force small enough not to damage the side flap according to a material used as the side flap, when temporarily fixing the fixing tape to the side flap.

The engaging portion forming the engaging region is provided on a surface of the side flap. On the other hand, the non-engaging portion is provided on either or both of the side flap surface and the fixing tape surface. For example, in a case where the fixing tape is folded back at a lateral edge of the side flap and the hook member overlaps with the fixing tape substrate as subsequently described, the non-engaging portion can be formed either only on an area where the hook member is overlapping with the fixing tape (FIG. 5), or over an area where the hook member is overlapping with both the fixing tape and the side flap (FIG. 6A). Also, in a case where the hook member does not overlap with the fixing tape substrate, the non-engaging portion is formed only on the side flap surface (FIG. 6B, FIG. 8 and FIG. 9).

(3) The disposal diaper according to either (1) or (2), wherein the fixing tape comprises a fixing tape substrate and the hook member provided on a surface of the fixing tape substrate; and the fixing tape substrate is provided with a thumb portion on an end portion thereof and an attaching portion on the other end portion thereof.

According to the present invention, the fixing tape comprises a fixing tape substrate and the hook member provided on a fixing tape surface of the substrate; and the hook member is disposed on the fixing tape substrate in such a manner that a thumb portion is provided on an end portion of the fixing tape substrate and an attaching portion is provided on the other end portion thereof. Therefore, although the fixing tape is temporarily fixed, with the hook member engaged with the engaging region on the side flap, the fixing tape can be easily separated by pulling the thumb portion. In addition, an engaging piece implanted with hook-shaped engaging elements or an engaging piece implanted with mushroom-shaped engaging elements can be employed as the hook member.

Here, the attaching portion means a portion where the fixing tape substrate is bonded to a surface of the side flap for fixing of the fixing tape. Also, the thumb portion means a portion disposed on an end portion of the fixing tape opposite from the attaching portion, to be grabbed when separating the fixing tape.

Also, according to (3) the hook member is disposed on the fixing tape substrate in such a manner that the attaching portion and the thumb portion are located at the respective sides of the fixing tape substrate, however, the hook member may be disposed over the entire attaching portion from the edge end of the attaching portion, only leaving the thumb portion uncovered. In this case, the hook member is overlapped with each other on the attaching portion surface when the fixing tape is folded back (FIG. 7).

Further, the fixing tape substrate may be comprised of a nonwoven fabric alone, a nonwoven fabric laminated with a film or the like, or a film laminated with a nonwoven fabric on both sides. Among those, it is preferable to employ a breathable material such as a nonwoven fabric, from the viewpoint of prevention of moist air residence. Also, as the hook member, a male engaging piece of a hook-and-loop fastener is preferably used because it can be repeatedly joined and separated.

(4) The disposable diaper according to (1) or (2), wherein the engaging region has an engaging force with the hook member in a range of 0.3 N/25 mm to 2.2 N/25 mm.

According to the present invention, since an engaging force of the hook member in the engaging region is 0.3 N/25 mm to 2.2 N/25 mm, there is no likelihood that the side flap surface is damaged when separating the fixing tape temporarily fixed thereto.

The fixing tape is temporarily fixed to the side flap surface when the hook member achieves engagement with the side flap surface. In this case, it is preferable that an engaging force between the hook member and the engaging region is in a range of 0.3 N/25 mm to 2.2 N/25 mm, for preventing damage to the side flap surface when separating the fixing tape. With the engaging force lower than 0.3 N/25 mm, the fixing tape cannot remain temporarily fixed through the attaching portion of the fixing tape substrate. By contrast, in a case where the engaging force is greater than 2.2 N/25 mm, the hook member and the engaging region become too tightly engaged and the side flap surface is prone to be pulled until it is damaged when separating the fixing tape. Moreover, since the temporarily fixed fixing tape has to be carefully separated so as not to tear the side flap when fitting the diaper onto a wearer, the operation becomes troublesome.

(5) The disposable diaper according to (2), wherein the non-engaging portion has an engaging force with the hook member not greater than 2.2 N/25 mm.

According to the present invention, the engaging force of the hook member with the non-engaging portion is not greater than 2.2 N/25 mm, which is equal to or lower than the engaging force in the engaging region. As a result, the fixing tape can be separated from the non-engaging portion with a force that is the same as or smaller than a force required to separate the fixing tape from the engaging region, which eliminates a trouble that may be incurred because of an excessive engaging force in separating the fixing tape from the non-engaging portion. Also, this engaging force can be appropriately determined in a range not greater than 2.2 N/25 mm depending on an engaging force in the engaging portion, so as to enable the fixing tape to be temporarily fixed to the side flap surface. In other words, in a case where an engaging force of the engaging portion is low and the fixing tape is not temporarily fixed tightly enough, it is desirable to increase an engaging force of the non-engaging portion so that the fixing tape can be temporarily fixed over the entire engaging region with a sufficient engaging force and, at the same time, the side flap surface can be prevented from being damaged.

(6) The disposable diaper according to (5), wherein the non-engaging portion is comprised of a nonwoven fabric having a low engaging force with the hook member.

According to the present invention, since the non-engaging portion is comprised of a nonwoven fabric having a low engaging force with the hook member, the fixing tape can be easily separated because of the weak engaging force with the hook member. Also, since the nonwoven fabric provided with a loop-shaped fiber on its surface is employed, the surface can serve as a female engaging piece. Further, because of the breathability of the nonwoven fabric, moist air does not reside where the fixing tape is attached. In addition, since the nonwoven fabric employed in the non-engaging portion is similar to the main material of the diaper, a consistent product image can be created.

(7) The disposable diaper according to (2), wherein an area of the engaging portion is in a range of 5% to 50% of the entirety of the hook member.

According to the present invention, since an area of the engaging portion of the engaging region is in a range of 5% to 50% of the entirety of the hook member, and such engaging portion makes contact with the side flap surface to achieve engagement, the engaging force of the hook member with the side flap surface is only modest. As a result, the temporarily fixed fixing tape can be separated with a small force, and the side flap surface is prevented from being damaged even when the side flap is comprised of an elastic material or a bulky nonwoven fabric. Here, in a case where an area of the hook member to be engaged with the side flap surface (engaging portion) is less than 5%, the fixing tape cannot remain temporarily fixed to the side flap surface because of the insufficient engaging force with the side flap surface. On the other hand, in a case where the engaging portion occupies more than 50% of the hook member, the hook member and the side flap surface becomes too tightly engaged to separate the fixing tape with ease, and the side flap surface becomes prone to be damaged, which is a disadvantage to be eliminated.

Also, in a subsequently described case where the hook member overlaps, upon folding back the fixing tape, with a portion of the fixing tape substrate thus comprising a non-engaging portion of the engaging region on the fixing tape substrate, an opening may be provided in the attaching portion of the fixing tape substrate to be engaged with the side flap surface, so that a portion of the side flap surface is exposed through the opening to comprise an engaging portion for achieving engagement with the hook member.

(8) The disposable diaper according to any one of (1) to (7), wherein the hook member of the fixing tape is a male engaging piece of a hook-and-loop fastener.

According to the present invention, since the hook member of the fixing tape is a male engaging piece of a hook-and-loop fastener, the hook member can be repeatedly joined and separated. Also, since the side flap is comprised of a nonwoven fabric, the hook member can be engaged with the loop-shaped fiber on the surface of the nonwoven fabric.

(9) The disposable diaper according to any one of (1) to (8), wherein the fixing tape is attached to an inner surface of the side flap and can be folded back at a lateral edge thereof in such a manner that its face having the hook member faces Inside, so as to be temporarily fixed to the side flap surface in a manner where the hook member achieves engagement in the engaging region when the fixing tape is folded back.

According to the present invention, the fixing tape is fixed on an inner surface of the side flap and can be folded back at a lateral edge thereof with its face having the hook member facing inside, so as to be temporarily fixed to the side flap surface in a manner where the hook member achieves engagement in the engaging region. Therefore, the fixing tape is not outwardly protruding from the lateral edge of the side flap of the diaper. As a result, in a manufacturing process of the diaper, when the diaper continuously moves along a manufacturing line to proceed with the steps of assembling various parts, folding, etc., the fixing tape does not get caught in a machine or hooked with another part of the diaper, therefore a smooth flow of production can be maintained. Further, the possibility of a failure such that an entire diaper gets caught in a machine is minimized.

Also, the engagement with the side flap is performed in the engaging region comprised of the engaging portion and the non-engaging portion, therefore the hook member is not entirely engaged with the side flap surface. Accordingly, the engaging force is reduced. Consequently, even in a case where a bulky elastic loop fiber fabric is used as the side flap for improving fitness of the diaper around the waist or legs of a wearer, the fixing tape temporarily fixed to the side flap can be separated with a small force and resultantly the side flap surface can be prevented from being damaged. On the other hand, when the diaper is applied to a wearer, since an entire surface of the hook member is engaged with the diaper surface a sufficient engaging force can be obtained, which retains the diaper in place. Further, the engaging force of the temporary fixing can be adjusted by appropriately controlling a ratio of the engaging portion and the non-engaging portion forming the engaging region. Here, the inner surface of the side flap means the surface that opposes the body of a wearer when the diaper is applied to the wearer.

(10) The disposable diaper according to any one of (1) to (8), wherein the fixing tape is attached to the side flap in such a manner that the hook member opposes the side flap surface, so that the fixing tape is temporarily fixed to the side flap surface in a manner where the hook member achieves engagement in the engaging region.

According to the present invention, the fixing tape is attached to the side flap with the hook member opposing the side flap surface, so that the fixing tape is temporarily fixed to the side flap surface by the engagement of the hook member on the fixing tape in the engaging region comprised of the engaging portion and the non-engaging portion. Therefore, the fixing tape is not outwardly protruding from the lateral edge of the side flap of the diaper. As a result, in a manufacturing process of the diaper, when the diaper continuously moves along a manufacturing line to proceed with the steps of assembling various parts, folding, etc., the fixing tape does not get caught in a machine or hooked with another part of the diaper, therefore a smooth flow of production can be maintained. Further, possibility of a failure such that an entire diaper gets caught in a machine is minimized.

Also, since the temporary fixing with the side flap surface is achieved by the engagement in the engaging portion of the engaging region, the engaging force with the side flap surface is only modest. Accordingly, even in a case where a bulky elastic nonwoven fabric is used as the side flap for improving fitness of the diaper around the waist or legs of a wearer, the fixing tape temporarily fixed to the side flap can be separated with a small force. As a result the side flap surface can be prevented from being damaged. On the other hand, when the diaper is fitted onto a wearer, since an entire surface of the hook member is engaged with the diaper surface a sufficient engaging force can be obtained, which retains the diaper in place. Further, the engaging force of the temporary fixing can be adjusted by appropriately controlling a ratio of the engaging portion and the non-engaging portion forming the engaging region.

(11) The disposable diaper according to any one of (1) to (8), wherein the fixing tape is attached to an outer surface of the side flap and can be folded back at a lateral edge thereof in such a manner that its face having the hook member faces inside, so as to be temporarily fixed to the side flap surface in a manner where the hook member achieves engagement in the engaging region after the fixing tape is folded back.

According to the present invention, the fixing tape is bonded to an outer surface of the side flap (the wearer's garment side when the diaper is fitted onto the wearer). And the fixing tape thus attached is folded back at a lateral edge of the side flap in such a manner that its face having the hook member faces inside, so as to be temporarily fixed to the side flap surface in a manner where the hook member achieves engagement in the engaging region when the fixing tape is folded back. Therefore, the fixing tape is not outwardly protruding from the lateral edge of the side flap of the diaper. As a result, in a manufacturing process of the diaper, when the diaper continuously moves along a manufacturing line to proceed with the steps of assembling various parts, folding, etc., the fixing tape does not get caught in a machine or hooked with another part of the diaper, therefore a smooth flow of production can be maintained. Further, the possibility of a failure such that an entire diaper gets caught in a machine is minimized.

Also, since the temporary fixing with the side flap is achieved by the engagement in the engaging region comprised of the engaging portion and the non-engaging portion, the engaging force is only modest. Therefore, even in a case where a bulky elastic loop fiber fabric is used as the side flap for improving fitness of the diaper around the waist or legs of a wearer, the fixing tape temporarily fixed to the side flap can be separated with a small force. As a result the side flap surface can be prevented from being damaged. On the other hand, when the diaper is fitted onto a wearer, since an entire surface of the hook member is engaged with the diaper surface a sufficient engaging force can be obtained, which retains the diaper in place. Further, the engaging force of the temporary fixing can be adjusted by appropriately controlling a ratio of the engaging portion and the non-engaging portion forming the engaging region.

(12) The disposable diaper according to any one of (9) to (11), wherein the non-engaging portion of the engaging region is formed on at least one of either the fixing tape and the side flap surface or the both thereof.

The non-engaging portion of the engaging region is formed at different positions depending on an attaching method of the fixing tape to the side flap surface or length of the hook member and so forth. For example, in a case where the fixing tape is attached to an inner surface of the side flap to be folded back at a lateral edge of the side flap with its face having the hook member facing inside, for temporary fixing as described in (9), the non-engaging region can be formed only on the fixing tape substrate, on both the fixing tape substrate and the side flap surface, or only on the side flap surface. Also, in a case where the fixing tape is attached to the side flap surface in such a manner that the hook member opposes the side flap surface so that the fixing tape is temporarily fixed in a manner where the hook member achieves engagement in the engaging region as described in (10), the non-engaging region can be formed either only on the side flap surface or on both the fixing tape substrate and the side flap surface. Further, in a case where the fixing tape is attached to an outer surface of the side flap to be folded back at a lateral edge of the side flap with its face having the hook member facing inside, for temporary fixing as described in (11), the non-engaging portion is formed only on the side flap surface (see FIGS. 5, 6A, 6B, 8 and 9).

(13) The disposable diaper according to any one of (9) to (11), wherein the engaging portion in the engaging region is formed on the side flap surface.

Since the side flap surface is comprised of a bulky nonwoven fabric, the loop-shaped fiber on a surface of the nonwoven fabric serves as a female engaging piece for the hook member, and resultantly a large engaging force can be obtained.

(14) The disposable diaper according to any one of (9) to (11), wherein the fixing tape substrate is comprised of a nonwoven fabric having a low engaging force with the hook member.

According to the present invention, since the fixing tape substrate is comprised of a nonwoven fabric having a low engaging force with the hook member, the fixing tape substrate serves as a non-engaging portion, as a result of which an engaging force, produced on the part where the hook member and the fixing tape substrate overlap, becomes low when the fixing tape attached to the side flap surface is folded back. Consequently, an additional process of forming a non-engaging portion on the fixing tape is not necessary.

(15) The disposable diaper according to (9), wherein the fixing tape is provided with an opening in the attaching portion.

According to the present invention, since an opening is provided in the attaching portion of the fixing tape, a portion of the side flap surface is exposed through the opening when the attaching portion is bonded and fixed to the side flap surface, therefore the hook member can be engaged with the exposed surface thus achieving the temporary fixing of the fixing tape to the side flap surface.

(16) The disposable diaper according to any one of (1) to (15), wherein the side flap comprises an elastic sheet and a nonwoven fabric combined thereto at least on the wearer's body side.

According to the present invention, since the side flap is elastic, a waist size can be adjusted to achieve a better fitting of the diaper onto a wearer. A disposable diaper of this type is designed to fasten a fixing tape provided on a side flap around the wearer's waist on the ventral side, upon fitting the diaper in an ordinary manner onto the wearer, therefore providing elasticity to the side flap enables the diaper to be fitted to different waist sizes.

(17) A disposable diaper comprising a fixing tape provided with a hook member, wherein an engaging region with which the hook member of the fixing tape is to be engaged includes therein a non-engaging portion where the hook member is substantially unable to be engaged, and the non-engaging portion comprises a temporary fixing portion of the fixing tape.

According to the present invention, the non-engaging portion where the hook member is substantially unable to be engaged, which is provided in a portion of the engaging region where the hook member of the fixing tape is to be engaged, comprises the temporary fixing portion of the fixing tape. Therefore, when the fixing tape is engaged with the engaging region via the hook member provided on the fixing tape, the fixing tape is not engaged with the entire surface of the engaging region but only with the portion except the non-engaging portion. As a result the engaging force of the temporary fixing is only modest, and the temporarily fixed fixing tape can be easily separated. Also, the engaging force of the temporary fixing can be adjusted as desired, by appropriately selecting a dimension of the engaging portion.

PREFERRED EMBODIMENTS OF THE INVENTION

The embodiment of the present invention will be described hereinafter referring to the accompanying drawings, however, it is to be understood that the present invention is not limited to the following embodiment.

Figure 1:
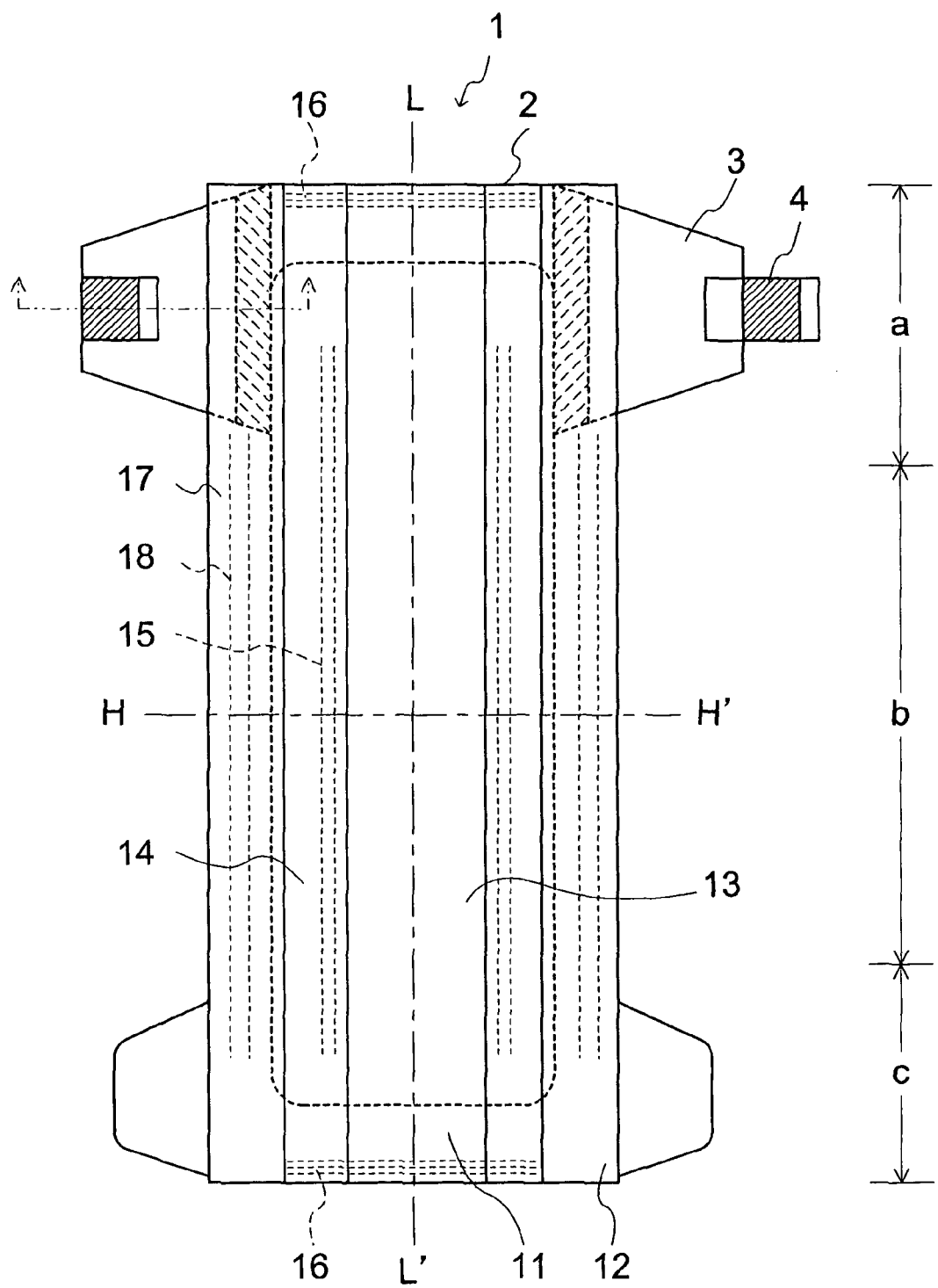
FIG. 1 is a plan view showing an unfolded disposable diaper according to the embodiment of the present invention.

FIG. 1 shows an unfolded view of a disposable diaper according to the present invention. This disposable diaper includes a first waist section a, a crotch area section b and a second waist section c.

Referring to FIG. 1 the disposable diaper 1 includes a diaper main body 2, a pair of side flaps 3 provided at the proximity of respective longitudinal end portions of the first waist section a and extending outwardly (along a direction of H-H' in the drawing) from the respective lateral end portions, and a fixing tape 4 disposed in proximity of a lateral edge farthest along the extension of the respective side flaps 3. The diaper main body 2 is provided with a liquid-permeable top sheet 11 to be in contact with a wearer's skin, a non-liquid-permeable back sheet 12 to face the wearer's garment side, an absorbent body 13 enclosed in these sheets in an overall rectangular form, an hourglass shape, etc., a three-dimensional gather section 14 provided on the top sheet generally along the respective longitudinal edges of the absorbent body, an elastic member 15 disposed along a longitudinal direction of the three-dimensional gather 14 (a direction of L-L') for providing elasticity to the three-dimensional gather 14, and an elastic member 16 disposed along the respective outer edges of the first waist section a and the second waist section b in a lateral direction of the diaper main body 2 (a direction of H-H' in the drawing) for providing elasticity to the waist sections. The top sheet 11 and the back sheet 12 are longer and wider than the absorbent body 13, and respectively extending outwardly over an outer edge thereof, thus comprising a leg gather 17 at least in the crotch area section b. Also an elastic member 18 is disposed along the leg gather to provide elasticity thereto.

Also, the side flap 3 is not a continuous section from the diaper main body 2, but a separate part joined thereto on a ventral or a dorsal side.

The side flap 3 is bonded and fixed in proximity of an edge of the first waist section a along a longitudinal direction of the diaper main body 2. The side flap 3 and the diaper main body 2 are bonded by a thermal method including heating and thermal press, such as heat seal, sonic seal, hot-melt adhesive, etc.

The absorbent body 13 serves to absorb and retain liquid excrement such as urine. It is preferable to employ a material that is bulky, shape-keeping and not chemically stimulative, as the absorbent body 13. Generally, one or a combination of at least two out of pulp, chemical pulp, rayon, acetate, natural cotton, a super absorbent polymer, a super absorbent polymer fiber and a synthetic fiber may be employed. The shape and structure of the absorbent body 13 may vary depending on requirements, while a total absorbing capacity of the absorbent body 13 should be determined in accordance with a designed insertion amount as a diaper and an intended application. The size and absorbing capacity of the absorbent body 13 varies according to the wearer's age from an infant up to an adult.

As the back sheet 12, it is preferable to employ a material capable of preventing leakage of excrement absorbed in the absorbent body 13. Also, employing a moisture-permeable material enables reduction of moist air residence during an application, thus alleviating discomfort of a wearer.

Examples of such material include a sheet film made by lamination of a synthetic resin, a breathable film obtained by filling an inorganic filler and drawing, a laminated material made in combination of paper, a nonwoven fabric and a film, a breathable non-liquid-permeable sheet having a porosity of 10 to 30% in which capillary tubes of a diameter of 0.1 to 0.6 mm are disposed toward the absorbent body, etc. It is also preferable to use a thermal processed film, embossed for providing a cloth-like appearance.

As the top sheet 11, it is preferable to employ a liquid-hydrophilic material that is not stimulative to human skin. One or a combination of at least two out of nonwoven fabrics manufactured by melt-blown process, spun bond, through-air, point bonding, needle punch, wet forming spun lace, foam film, etc., may be cited as examples of such material. Also, among fiber sheets, one or a combination in a form of a core and sheath structure, or a further combination thereof formed in a sheet may be used, out of rayon, acetate, cotton, pulp or a synthetic resin.

The side flap 3 is comprised of a layer of elastic sheet 31 laminated with a nonwoven fabric 32 on its both faces. The formation of such side flap 3 can be performed by lamination, thermal process, ultrasonic or mechanical bonding, etc. Elastomers to be joined include, for example, sheet-formed polymer such as polyurethane, styrene-butadiene-styrene block copolymer (SBS), styrene-butadiene-ethylene-styrene block copolymer (SBES), styrene-isoprene-styrene block copolymer (SIS), or a net or a filiform elastic member composed of these copolymers. Also, for joining an elastic sheet and a nonwoven fabric, it is also possible to confound an ultrasonic process, hot-melt, needle punch, high-pressure fluid process, etc., in addition to bonding by heating or thermal press. Further, a the composition of the side flap 3 is not limited to this embodiment, but can also be one layer each of the elastic sheet and the nonwoven fabric, or a plurality of layers of the same.

Also, the elastic sheet 31 is a group of an elastically resilient fiber, and is elastically expandable at least in one direction. A continuous fiber of a diameter of 0.1 to 50 µm, preferably 0.5 to 30 µm, composed of a thermal plastic elastic polymer such as styrene type elastomer or urethane is preferably employed. A group of such fiber is, for example, a multitude of continuous fibers continuously extruded by a direct spinning method such as a spun bond or melt-blown process. Further, a thermal bonded nonwoven fabric or a film composed of a thermal plastic elastic polymer may also be employed.

On the other hand, a nonwoven fabric manufactured by spun bond, point bond, through-air bond, chemical bond, melt-blown, spun lace or needle punch etc., may be used as the nonwoven fabric 32. As a material fiber, a core and sheath type composite fiber or a side-by-side type composite fiber of a polyolefin type, polyester type, polyamide type, or polyethylene/polypropylene or polyethylene/polyester can be employed. A typical example of such nonwoven fabric is a group of expandable continuous fiber that is non-elastically expandable in an expanding direction of the elastic sheet. This continuous fiber has a diameter of 0.1 to 50 µm, preferably 0.5 to 30 µm, and is composed of one or a combination of at least two out of polyethylene, polypropylene, ethylene-propylene copolymer, ethylene-propylene-butene copolymer, and a composite fiber of these. A specific weight of the nonwoven fabric is in a range of 2 to 100 g/m$^2$, desirably 7 to 20 g/m$^2$, and a group of the nonwoven fabric can be obtained through irregularly accumulating a multitude of continuous fibers continuously extruded by a popular direct spinning method such as a spun bond or melt-blown process on a belt conveyer running in one direction.

For reference sake, the elastic side flap employed in the embodiment of the present invention is made of "flexAir" manufactured by Tredegar Corporation. This nonwoven fabric is comprised of three layers including two layers of nonwoven fabric having a specific weight of 18 g/m$^2$, with an elastic film of a specific weight of 75 g/m$^2$ is interleaved therebetween and bonded by an ultrasonic seal method. This elastic side flap has stress characteristics of 1200 to 1600 mN at 75% expansion, 500 to 900 mN at 50% expansion and 200 to 450 mN at 30% expansion, in reverse stress at a second cycle of 100% expansion.

Figure 2:
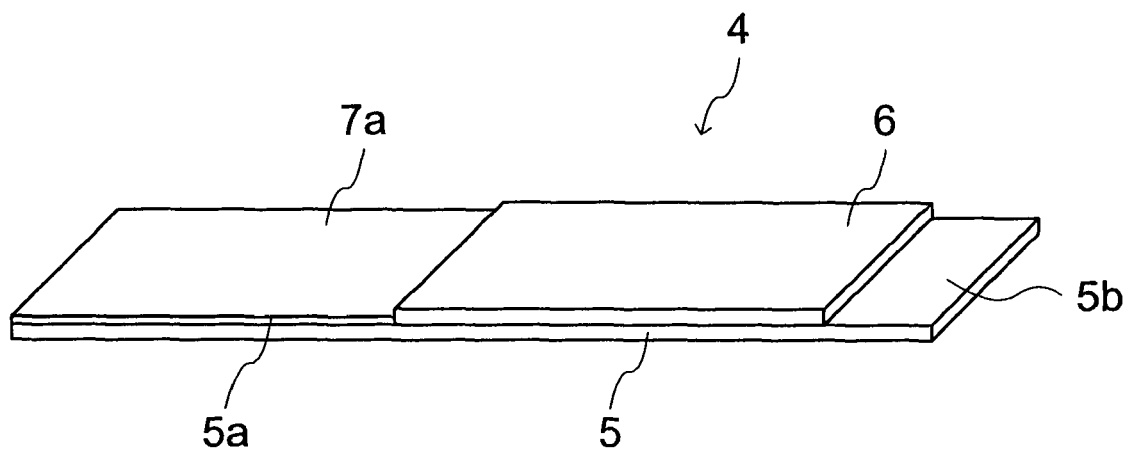
FIG. 2 is a schematic perspective view showing a fixing tape used in the disposable diaper according to the embodiment of the present invention.

The fixing tape 4 serves to fix the disposable diaper 1 around the waist section so that the diaper does not fall off, upon fitting the diaper onto a wearer. Referring to FIG. 2, the fixing tape 4 is comprised of a ribbon-shaped fixing tape substrate 5 composed of one or a combination of nonwoven fabrics manufactured by melt-blown, spun bond, point bond, through-air, needle punch, spun lace etc., and a hook member 6 disposed on a surface (upper face in the drawing) of the fixing tape substrate 5. The hook member 6 is disposed between an attaching portion 5a and a thumb portion 5b so as to leave uncovered attaching portion 5a at an end portion of the fixing tape substrate and the thumb portion at the other end portion thereof. Also, the attaching portion 5a is provided with a non-engaging portion 7a that does not become engaged with the hook member. As the hook member 6, an engaging piece implanted with hook-shaped engaging elements or an engaging piece implanted with mushroom-shaped engaging elements may be employed. Also, a nonwoven fabric, a film sheet such as a polyethylene film or a polypropylene film, or a nonwoven fabric melt-hardened by a thermal or an ultrasonic process may be employed as the non-engaging portion 7a, which is formed on an upper surface (upper side of the drawing) of the attaching portion 5a. Further, the non-engaging portion 7a may be formed on the attaching portion 5a of the fixing tape 4 after the fixing tape 4 is attached to the side flap 3, instead of forming in advance on the fixing tape 4. Otherwise, it is also possible to employ as a material of the fixing tape substrate 5, a nonwoven fabric having an engaging force with the hook member 6 as low as 2.2 N/25 mm or less, a material that has a weak engaging force or no engaging force at all with the hook member, including a film sheet such as a polyethylene film or a polypropylene film, or a nonwoven fabric melt-hardened by a thermal or an ultrasonic process. In a case where one of these materials is used as the fixing tape substrate, it is not necessary to form a non-engaging portion since the fixing tape substrate itself has a low engaging force with the hook member. Accordingly, it is preferable to employ a material having a low engaging force with the hook member as the fixing tape substrate 5, from the viewpoint of omitting the additional process of forming the non-engaging portion. In addition, the non-engaging portion 7a can be made of a material that can barely be engaged, or cannot be engaged at all, i.e. that is substantially unable to be engaged with the hook member.

An example of a fixing tape made of a fixing tape substrate 5 that has a weak engaging force with the hook member can be specifically comprised of a nonwoven fabric "PK116" (specific weight 80 g/m$^2$) manufactured by Mitsui Chemicals, Inc. as the fixing tape substrate, and "CS600" Article No. 1600 ppi manufactured by Sumitomo 3M Limited as the hook member (male engaging piece), attached on a surface of the fixing tape substrate.

Figure 3:
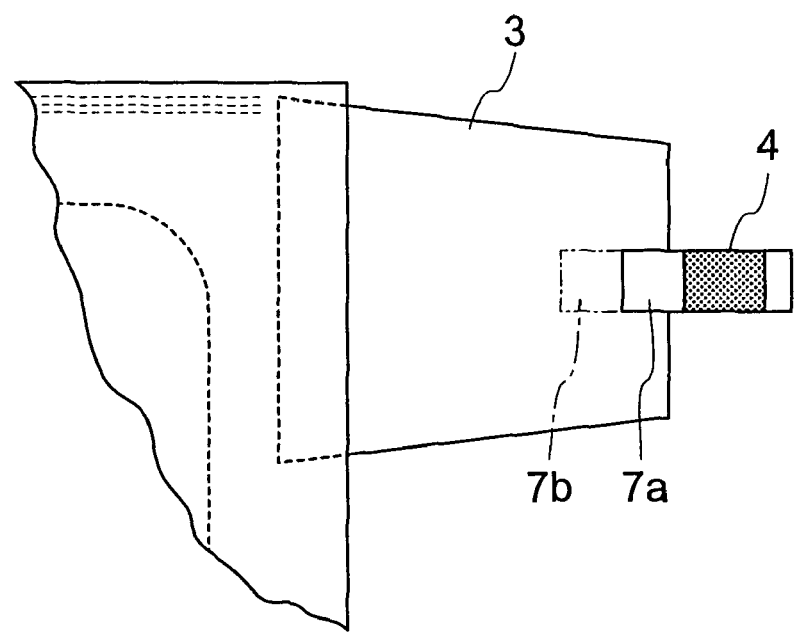
FIG. 3 is a fragmentary enlarged view showing a portion where the fixing tape is attached to a side flap of the disposable diaper according to the embodiment of the present invention.
Figure 4:
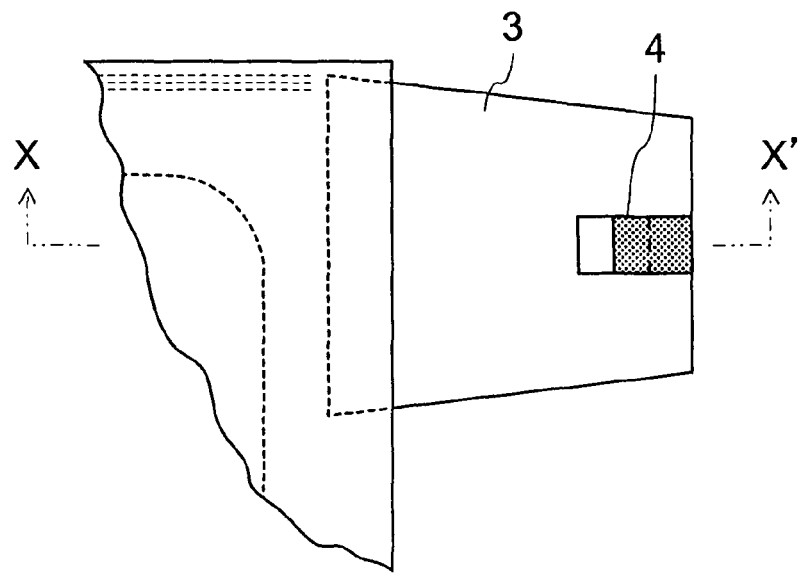
FIG. 4 is a fragmentary enlarged view showing the same portion as FIG. 3 but in a state where the fixing tape is folded back toward the side flap and temporarily fixed.
Figure 5:
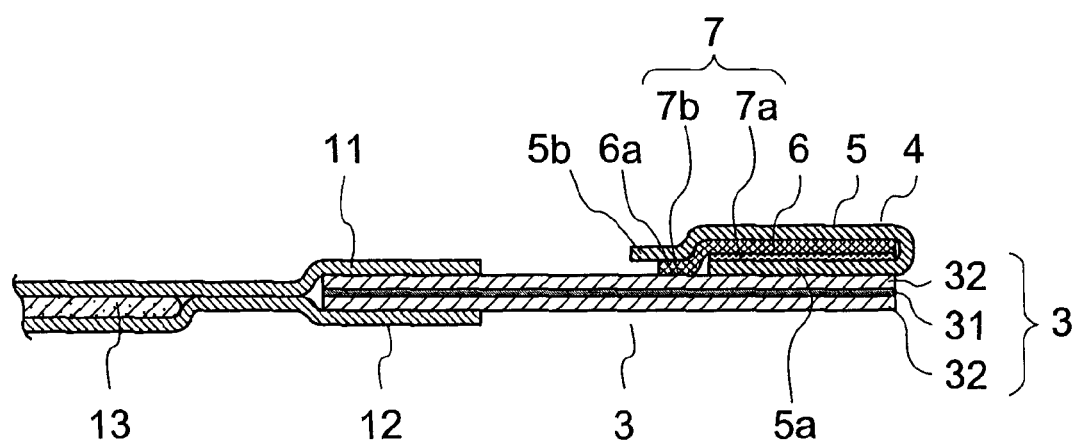
FIG. 5 is a schematic cross-sectional view taken along the line X-X' of FIG. 4.

Referring to FIG. 3, the fixing tape 4 is bonded and fixed to the side flap 3 by its attaching portion 5a on the fixing tape substrate 5, so as to extend outwardly from the proximity of a farthest lateral edge of the side flap 3. The non-engaging portion 7a, which does not become engaged with the hook member is provided on the attaching portion 5a, adjacent to which an engaging portion 7b to be engaged with the hook member 6 is provided on the side flap 3. The fixing tape 4 is folded back toward the side flap 3 at the lateral edge of the side flap 3, as shown in FIG. 4 and FIG. 5. Then, the fixing tape 4 is temporarily fixed to the side flap 3 in a manner where the hook member 6 becomes engaged with an engaging region 7 comprised of the non-engaging portion 7a of the fixing tape substrate 5 and the engaging portion 7b of the side flap 3.

FIG. 4 is a fragmentary enlarged view showing a state where the fixing tape 4 is folded back at the lateral edge of the side flap 3, and FIG. 5 is a cross-sectional view taken along the line X-X' of FIG. 4. As shown in FIG. 5, when the fixing tape 4 is folded back, the hook member 6 overlaps with the attaching portion 5a on the fixing tape substrate 5, with a portion of the hook member 6 protruding from the attaching portion 5a, and this protruding portion makes contact with the side flap 3 (hereinafter, this protruding portion is referred to as "protruding portion 6a"). The attaching portion 5a comprises the non-engaging portion 7a of the engaging region 7 and a portion of the side flap 3 with which the protruding portion 6a is engaged comprises the engaging portion 7b of the engaging region 7. Accordingly, by the engagement of the hook member 6 with the engaging portion 7b of the side flap 3, the fixing tape 4 is temporarily fixed. It is preferable that the engaging portion 7b with which the protruding portion 6a is to be engaged corresponds to 5 to 50% of the entire area of the hook member 6. In a case where the engaging portion 7b is smaller than 5% a sufficient engaging force cannot be obtained to retain the fixing tape temporarily fixed in position. By contrast, in a case where the engaging portion 7b is larger than 50%, an excessive engaging force is created because of the excessively large area for engagement. In such a case, a strong force is required to separate the temporarily fixed fixing tape 4 and the side flap surface is prone to damage.

Figure 10:
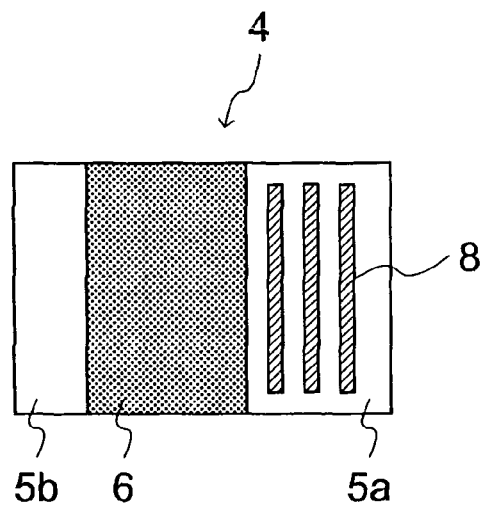
FIG. 10A is a plan view showing another embodiment of the fixing tape to be used in the disposable diaper according to the embodiment of the present invention.
FIG. 10B is a plan view showing another embodiment of the fixing tape to be used in the disposable diaper according to the embodiment of the present invention.
FIG. 10C is a plan view showing another embodiment of the fixing tape to be used in the disposable diaper according to the embodiment of the present invention.
Figure 10:
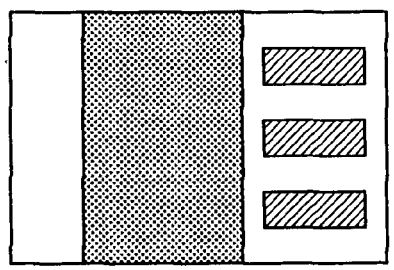
Figure 10:
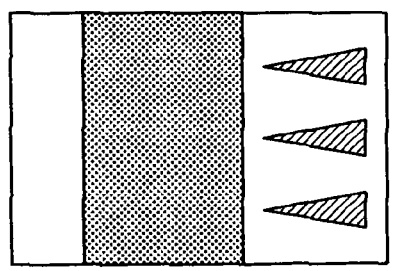
Figure 11:
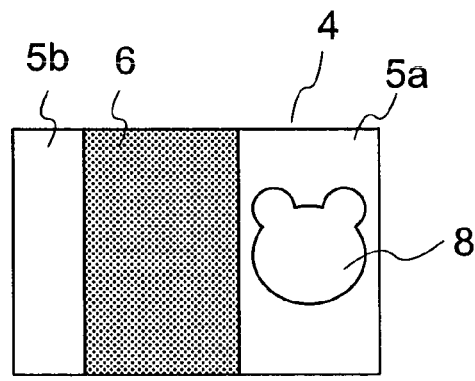
FIG. 11A is a plan view showing another embodiment of the fixing tape to be used in the disposable diaper according to the embodiment of the present invention.
FIG. 11B is a plan view showing another embodiment of the fixing tape to be used in the disposable diaper according to the embodiment of the present invention.
FIG. 11C is a plan view showing another embodiment of the fixing tape to be used in the disposable diaper according to the embodiment of the present invention.
FIG. 11D is a plan view showing another embodiment of the fixing tape to be used in the disposable diaper according to the embodiment of the present invention.
Figure 11:
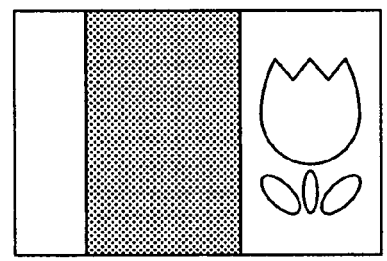
Figure 11:
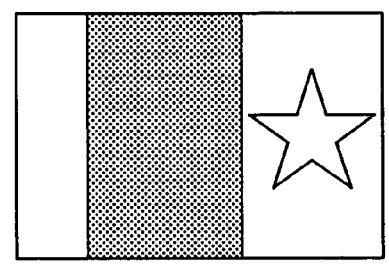
Figure 11:
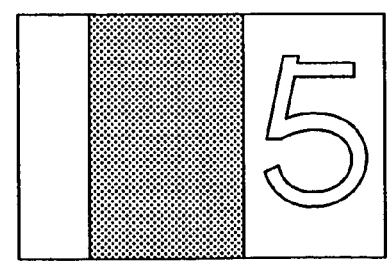

Also, in order to put the hook member 6 in contact with the side flap 3 to achieve engagement, it is also possible to provide an opening 8 of a rectangular or triangular shape in the attaching portion 5a of the fixing tape 4 as shown in FIG. 10A to FIG. 10C, instead of providing the engaging portion 7b for engagement with the protruding portion 6a. Further the opening 8 may be in a form of an illustrational design or a numeral as shown in FIG. 11A to FIG. 11D. As a result of providing such opening 8, when the fixing tape 4 is attached to the side flap 3 by its attaching portion 5a, a portion of the side flap surface is exposed through the opening 8. Accordingly, the hook member 6 is engaged with the exposed side flap surface, so that the fixing tape 4 can be temporarily fixed. Furthermore, a shape of the opening 8 is not limited to those shown in FIG. 10A to FIG. 10C and FIG. 11A to FIG. 11D. Also, the engagement of the hook member 6 may be achieved with either or both of the engaging portion 7b and the opening 8.

It is preferable that an engaging force of the hook member 6 in the engaging region 7 is in a range of 0.3 to 2.2 N/25 mm, according to a separating force measurement method to be subsequently described. With an engaging force lower than 0.3 N/25 mm the fixing tape cannot be temporarily fixed, while with an engaging force greater than 2.2 N/25 mm, it becomes difficult to separate the fixing tape 4 because of the excessive engaging force, and the side flap 3 may be damaged.

Also, when the fixing tape 4 is folded back, the hook member 6 overlaps with the attaching portion 5a, to be engaged with the engaging region 7 comprised of the non-engaging portion formed on the fixing tape substrate 5 and the engaging portion 7b formed on the side flap 3. In this case, it is preferable that an engaging force at the non-engaging portion 7a is not greater than 2.2 N/25 mm by the same measurement method as the engaging force of the side flap 3. In a case where the engaging force in this portion is greater than 2.2 N/25 mm, it becomes difficult to separate the fixing tape 4 despite the fixing tape being easily separated at the engaging region 7b, because the engaging force at the non-engaging portion 7a is excessive, and the operation of fitting the diaper becomes troublesome. Moreover, the side flap may be damaged where the fixing tape is attached.

Figure 6:
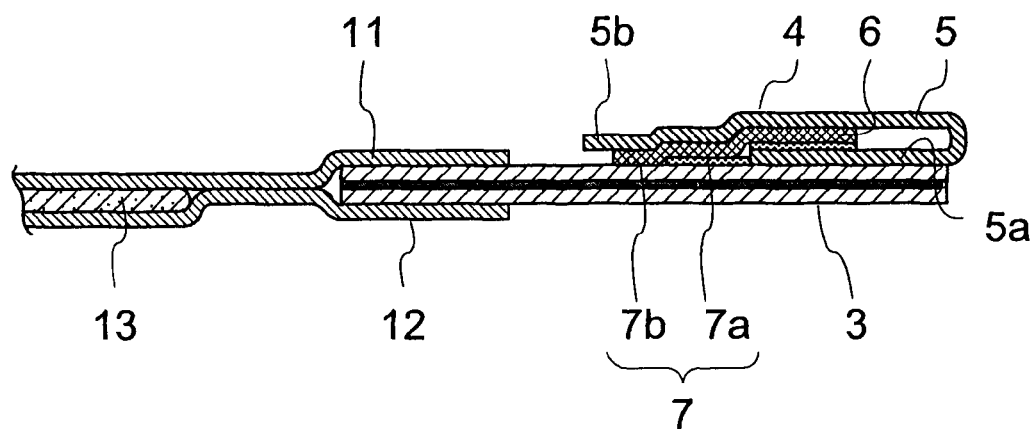
FIG. 6A is a schematic cross-sectional view showing another embodiment of FIG. 5, wherein an engaging region is formed over both the fixing tape substrate and the side flap surface.
FIG. 6B is a schematic cross-sectional view showing still another embodiment of FIG. 5, wherein the engaging region is formed only on the side flap surface.
Figure 6:
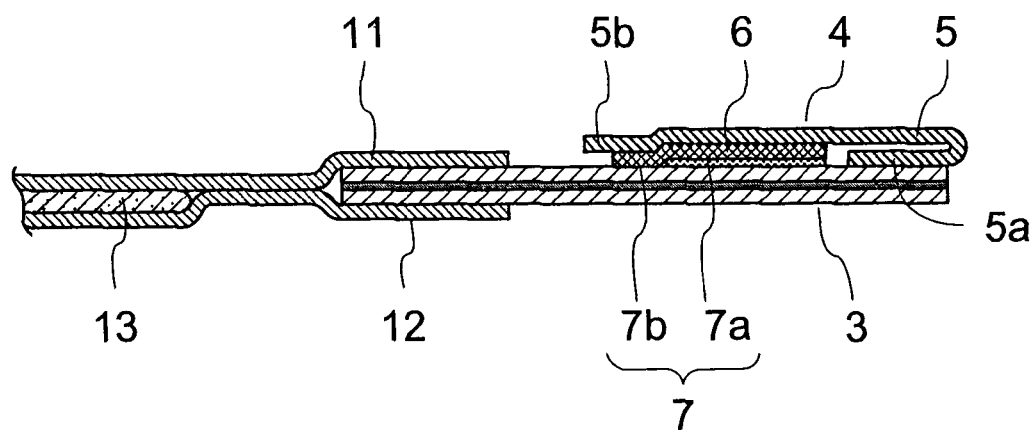

Further, a composition of the engaging region 7 including the non-engaging portion 7a and the engaging portion 7b is not limited to the combination of the non-engaging portion 7a on the fixing tape substrate 5 and the engaging portion 7b on the side flap 3 as already described. For example, in a case where, upon folding back the fixing tape 4 so that the hook member 6 overlaps with the attaching portion 5a of the fixing tape substrate 5 as well as with a portion of the side flap 3, the protruding portion of the hook member 6 over the side flap 3 is long enough, the non-engaging portion 7a can be formed on the attaching portion 5a of the fixing tape substrate 5 and a portion of the side flap 3 adjacent to the attaching portion 5a, as shown in FIG. 6A. Also, in a case where the hook member 6 makes contact in its entirety with the side flap 3 without overlapping with the attaching portion 5a of the fixing tape substrate 5 as shown in FIG. 6B, the non-engaging portion 7a is formed on the side flap 3. Such non-engaging portion 7a can be appropriately defined in the engaging region 7 with which the hook member 6 is to be engaged, in such a manner that an area of the engaging portion 7b becomes 5 to 50% of the entire area of the hook member, in accordance with the shape and attaching position of the fixing tape. Also, examples of a material for the non-engaging portion 7a include a nonwoven fabric having an engaging force with the hook member 6 as low as 2.2 N/25 mm or less, a film sheet such as a polyethylene film or a polypropylene film, or a nonwoven fabric melt-hardened by a thermal or an ultrasonic process.

Figure 7:
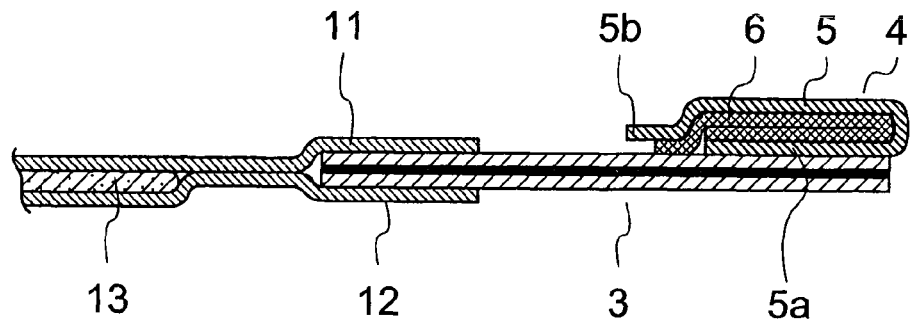
FIG. 7 is a schematic cross-sectional view of still another embodiment of FIG. 5, showing another embodiment of the fixing tape.

Furthermore, according to FIG. 2 the hook member 6 of the fixing tape 4 is disposed between the attaching portion 5a and the thumb portion 5b, however, the hook member 6 may also be disposed so as to cover an area from an end portion of the fixing tape substrate 5 comprising the attaching portion 5a to the thumb portion 5b. In a case where the fixing tape 4 with such a hook member 6 is fixed to the side flap 3 and folded back at a lateral edge of thereof, the hook member 6 overlaps with itself and still a portion of the hook member 6 makes contact with the side flap surface to be engaged therewith, as shown in FIG. 7. In this case too, it is preferable that an area of the hook member 6 to be in contact with the side flap surface is in a range of 5 to 50% of the entire area where the hook member 6 is to overlap. In addition, providing a folding slit on the hook member 6 at a position corresponding to the attaching portion 5a makes it easier to fold back the fixing tape 4.

Bonding and fixing of the fixing tape substrate 5 and the hook member 6 can be performed by heat seal, ultrasonic seal, hot-melt adhesive, etc. Examples of an elastomer used for bonding include polyurethane, styrene-butadiene-styrene block copolymer (SBS), styrene-butadiene-ethylene-styrene block copolymer (SBES), styrene-isoprene-styrene block copolymer (SIS).

Figure 8:
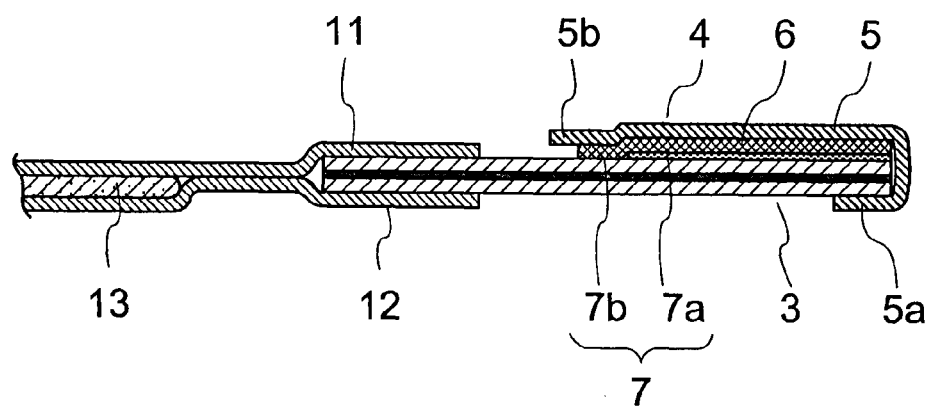
FIG. 8 is a schematic cross-sectional view showing a second embodiment of a portion where the fixing tape is attached to the side flap, in the disposable diaper according to the embodiment of the present invention.

Now, FIG. 8 shows a second embodiment of a part where the fixing tape 4 is attached to the side flap 3. FIG. 8 is a cross-sectional view of such a second embodiment, in which the fixing tape 4 is bonded and fixed to the proximity of a lateral edge of a back face of the side flap 3 by the attaching portion 5a, with the hook member 6 on the fixing tape 4 facing upward so as to oppose the side flap 3 when the fixing tape 4 is folded back and with the thumb portion 5b of the fixing tape 4 disposed at an outer side (right hand direction in the drawing) from the side flap 3.

Also, the engaging region 7 where the fixing tape 4 is to be engaged is formed on the side flap 3. A ratio of the non-engaging portion 7a and the engaging portion 7b in the engaging region 7 is set so that the engaging portion 7b is in a range of 5 to 50% of the entire hook member 6 as already described. Examples of a material to comprise the non-engaging portion include, as described above, a nonwoven fabric having a low engaging force with the hook member 6, a film sheet such as a polyethylene film or a polypropylene film, or a nonwoven fabric melt-hardened by a thermal or an ultrasonic process.

Then, the fixing tape 4 attached to the side flap 3 is folded back at a lateral edge of the side flap 3 toward the diaper main body 2 (left hand direction in the drawing), so as to be temporarily fixed to the side flap 3 in a manner where the hook member 6 on the fixing tape 4 becomes engaged with the engaging region 7.

Figure 9:
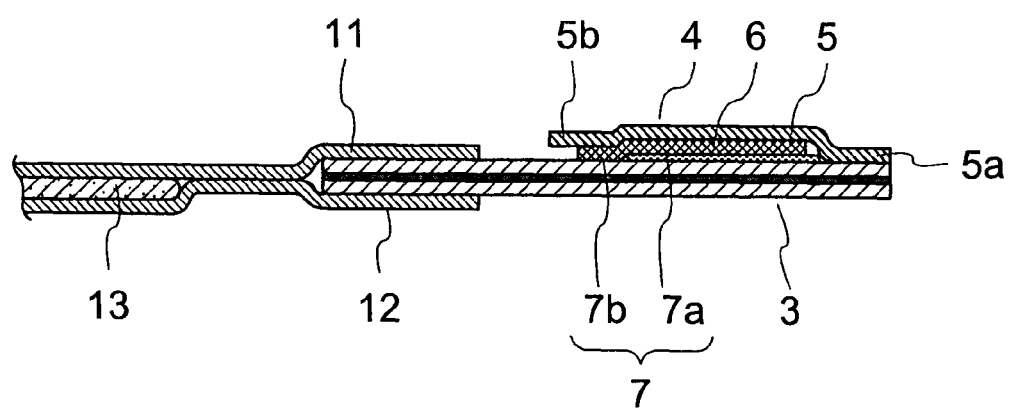
FIG. 9 is a schematic cross-sectional view showing a third embodiment of a portion where the fixing tape is attached to the side flap, in the disposable diaper according to the embodiment of the present invention.

Now, FIG. 9 shows a third embodiment of a part where the fixing tape 4 is attached to the side flap 3. FIG. 9 is a cross-sectional view of such a third embodiment, in which the fixing tape 4 is bonded and fixed to the proximity of a lateral edge of the side flap 3 by the attaching portion 5a, with the hook member 6 on the fixing tape 4 opposing the side flap 3 and with the thumb portion 5b of the fixing tape 4 extends toward the diaper main body 2 (left hand direction in the drawing).

Also, the engaging region 7 where the fixing tape 4 is to be engaged is formed on the side flap 3. A ratio of the non-engaging portion 7a and the engaging portion 7b in the engaging region 7 is set so that the engaging portion 7b is in a range of 5 to 50% of the entire hook member 6 as already described. Examples of a material to comprise the non-engaging portion include, as described above, a nonwoven fabric having a low engaging force with the hook member 6, a film sheet such as a polyethylene film or a polypropylene film, or a nonwoven fabric melt-hardened by a thermal or an ultrasonic process.

<Separating Force Measurement>

Figure 12:
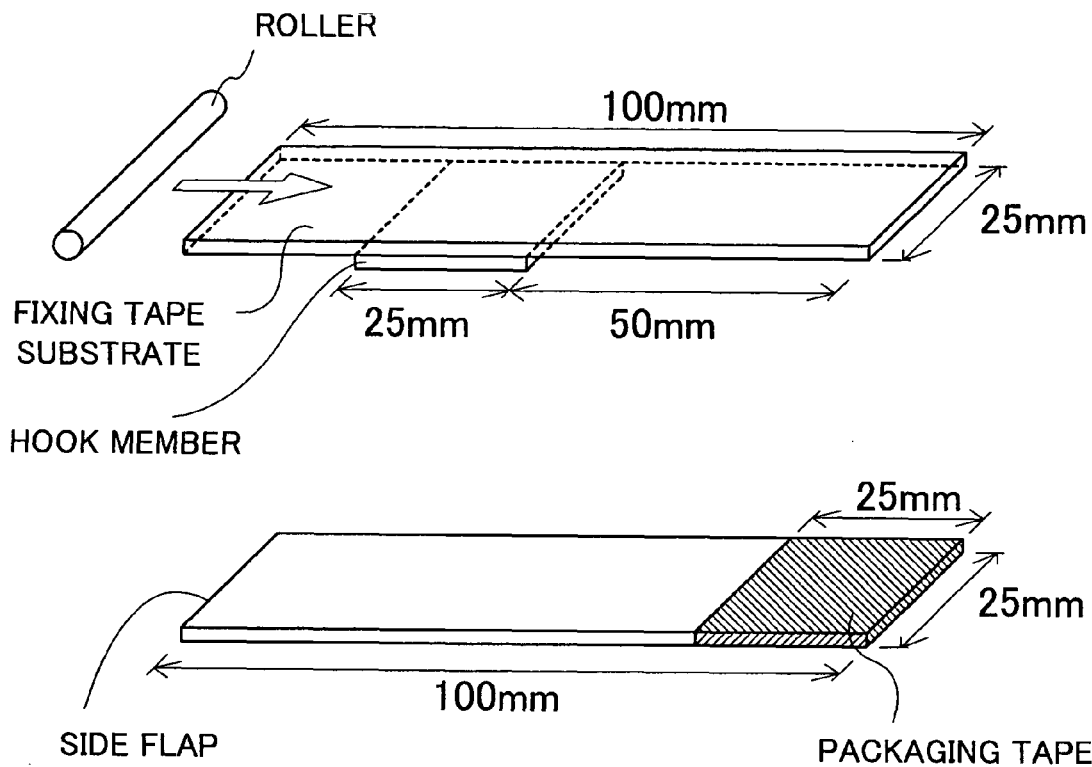
FIG. 12 is an explanatory drawing for explaining a making-up method of a sample piece for separating force measurement.
Figure 13:
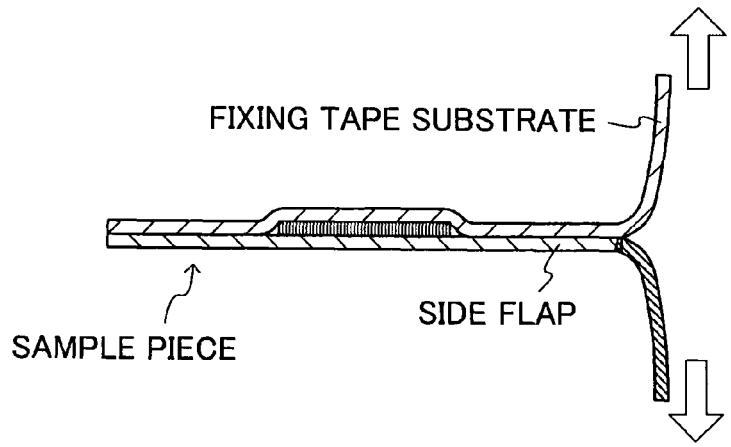
FIG. 13 is an explanatory drawing for explaining a separating direction in the separating force measurement.

As shown in FIG. 12, a side flap and a fixing tape substrate are respectively cut into a piece of 100 mm long×25 mm wide, and marked at every 25 mm in the longitudinal direction. Also, a hook member (male engaging piece of a hook-and-loop fastener) is cut into a piece of 25 mm×25 mm and fixed on the fixing tape substrate in a portion of 25 mm to 50 mm from an end portion thereof, with a double-sided adhesive tape. Meanwhile, the side flap is reinforced by winding a tape, for example, a packaging tape over 25 mm from an end portion. Then the fixing tape substrate is disposed over the side flap, in such a manner that the hook member opposes the side flap. A roller of 700 grams in weight is rolled over an upper face of the fixing tape substrate at a speed of 5 mm/sec, so that the hook member becomes engaged with the side flap, thus to comprise a test piece. An end portion of the fixing tape substrate and the portion reinforced with the packaging tape of the side flap of such a test piece are grabbed by a chuck, to be separated in a direction of the arrow in FIG. 13 at a pulling speed of 100 mm/sec by a measuring apparatus (INSTTRON 5564), and a maximum load was measured.

Materials employed in the separating force measurement were a nonwoven fabric "flexAir" from Tredegar Corporation (a composite material of a bulky nonwoven fabric layer of a specific weight of 25 g/m$^2$ and an elastomer layer of a specific weight of 75 g/m$^2$) for the side flap; a hook-and-loop fastener, Magic Tape (registered trademark) (male engaging piece) CS600 1600 ppi from Sumitomo 3M Limited for the hook member; and a nonwoven fabric of a specific weight of 80 g/m$^2$, PK116 from Mitsui Chemicals, Inc. for the fixing tape substrate.

The disposable diaper according to the present invention and the fixing tape incorporated therein have been described in detail as above referring to the drawings showing the embodiments, however, it is to be understood that the present invention is not limited to those illustrated examples; that various changes and modifications can be made without deviating from the spirit of the present invention; and that such changes and modifications are within the technical scope of the present invention.

In a disposable diaper comprising a diaper main body including a top sheet, a back sheet and an absorbent body enclosed in the sheets; a pair of side flaps disposed along the longitudinal end portion of the diaper main body; and a fixing tape disposed in proximity of a lateral edge of the respective side flaps; wherein the fixing tape is provided with a hook member; and the fixing tape and the side flap are to be engaged via the hook member, a region on the side flap where the fixing tape is to be engaged (engaging region) is comprised of an engaging portion with which the hook member can be engaged and a non-engaging portion with which the hook member can barely be engaged or cannot be engaged at all. The fixing tape attached to the side flap is folded back at a lateral edge thereof in such a manner that its face having the hook member faces inside, so as to be temporarily fixed to the side flap in a manner where the hook member achieves engagement in the engaging region on the side flap. Therefore, the fixing tape is not outwardly protruding from the lateral edge of the side flap of the diaper. As a result, in a manufacturing process of the diaper, when the diaper continuously moves along a manufacturing line to proceed with the steps of assembling various parts, folding, etc., the fixing tape does not get caught in a machine or hooked with another part of the diaper, therefore a smooth flow of production can be maintained. Further, the possibility of a failure such that an entire diaper gets caught in a machine is minimized. Furthermore, since the hook member is not exposed on the diaper surface, a wearer or a carer handling the diaper can be prevented from being hurt by the hook member.

Also, since the temporary fixing of the fixing tape and the side flap is performed in the engaging portion in the engaging region, the engaging force can be controlled by adjusting a ratio of the engaging portion. As a result, an engaging force can be adjusted in accordance with a material of the side flap, and the side flap can be prevented from being damaged.

Further, since the fixing tape substrate surface, to overlap with the hook member when the fixing tape is folded back, is provided with a non-engaging portion having a low engaging force with the hook member, an engaging force at this portion is also low, specifically the same as or lower than an engaging force between the side flap and the hook member, and resultantly the side flap can be prevented from being damaged around the point where the fixing tape is attached, when separating the fixing tape. Moreover, handling of the diaper can be performed free from trouble.

Furthermore, since a piece of fixing tape substrate is attached inside an elastic side flap, the composition and joining method of the fixing tape is quite simple, and as a result high production efficiency and a cost saving effect can be accomplished.

What is claimed is:

1. A disposable diaper, comprising:
a diaper main body including a top sheet, a back sheet and an absorbent body disposed between said top sheet and back sheet;
a pair of side flaps respectively extending outwardly in a lateral direction of said diaper main body from respective side edge portions of said diaper main body, the side flaps being disposed between said top sheet and back sheet, each of said side flaps comprising an elastic sheet sandwiched between upper and lower non-woven fabric layers; and
a pair of fixing tapes each of which has
a hook member, and
an attaching portion that is directly attached to a surface of one of said side flaps in a vicinity of an outermost lateral edge of said side flap, and
wherein
each of the fixing tapes is folded along the outermost lateral edge of said side flap with said hook member facing said surface of said side flap and being releasably, temporarily fixed to an engaging region on the surface of said side flap,
said fixing tape is provided with a rectangular slit in said attaching portion; and
a portion of said surface of said side flap, as the engaging region for temporarily, releasably fixing the surface of said flap to the fixing tape, is exposed through said rectangular slit and is directly mechanically, non-adhesively engaged with said hook member of the fixing tape being folded along the outermost lateral edge of the respective side flap.

2. The disposable diaper according to claim 1, wherein an engaging force of said engaging region with said hook member is in a range of 0.3 N/25 mm to 2.2 N/25 mm.

3. The disposable diaper according to claim 1, wherein said engaging region, defined by a non-woven fabric that has no adhesive on said surface, comprises
an engaging portion directly, mechanically, releasably and non-adhesively engaged with said hook member of the fixing tape being folded along the outermost lateral edge of the respective side flap, and
a non-engaging portion with which said hook member of the fixing tape being folded along the outermost lateral edge of the respective side flap is directly contactable and has an engaging force not greater than 2.2 N/25 mm.

4. The disposable diaper according to claim 1, wherein said hook member of said fixing tape is a male engaging piece of a hook-and-loop fastener.

5. A disposable diaper, comprising:
a diaper main body including a topsheet, a backsheet and an absorbent body disposed between said topsheet and backsheet;
a pair of side flaps respectively extending outwardly from an end portion of said diaper main body in a lateral direction of said diaper main body; and
a pair of fixing tapes each being directly attached to a surface of one of said side flaps in a vicinity of an outermost lateral edge of said side flap and being folded along the outermost lateral edge of the side flap;
wherein
said fixing tape is provided with a hook member;
each said side flap and the respective fixing tape being folded along the outermost lateral edge of the side flap are releasably engaged with each other through the hook member;
an engaging region is provided on the surface of each said side flap where the hook member of the respective fixing tape is releasably engageable for temporarily fixing said fixing tape to said side flap before use, said engaging region being defined by a non-woven fabric that has no adhesive on said surface;
an entire area of said engaging region is in a range of 5% to 50% of the entire area of said hook member;
said fixing tape comprises (i) a fixing tape substrate, (ii) said hook member provided on a surface of said fixing tape substrate, (iii) a gripping portion at one of opposite ends of the fixing tape substrate and adjacent to the hook member, and (iv) an attaching portion at the opposite end of the fixing tape substrate, said attaching portion being directly attached to said surface of said side flap; and
said fixing tape is provided with a slit extending though said attaching portion,
a portion of said surface of said side flap, as the engaging region for temporarily fixing the surface of said flap to the fixing tape, is exposed though said slit and is directly mechanically, non-adhesively engaged with said hook member of the fixing tape being folded along the outermost lateral edge of the respective side flap.

6. The disposable diaper according to claim 5, wherein an engaging force of said engaging region with said hook member is in a range of 0.3 N/25 mm to 2.2 N/25 mm.

7. The disposable diaper according to claim 5, wherein said engaging region comprises
an engaging portion with which said hook member of the respective fixing tape being folded along the outermost lateral edge of the side flap is directly, mechanically and non-adhesively engaged, and
a non-engaging portion with which the hook member of the fixing tape being folded along the outermost lateral edge of the respective side flap is directly contactable and has an engaging force not greater than 2.2 N/25 mm.

8. A disposable diaper, comprising:
a diaper main body including a top sheet, a back sheet and an absorbent body disposed between said top sheet and back sheet;
a pair of side flaps respectively extending outwardly in a lateral direction of said diaper main body from respective side edge portions of said diaper main body, each of the side flaps having opposite inner and outer surfaces adapted to face toward and away from a wearer, respectively, when the diaper is being worn on the wearer; and
a pair of fixing tapes each comprising:
a fixing tape substrate having opposite ends
a hook member on said fixing tape substrate,
a gripping portion defined by one of opposite ends of the fixing tape substrate and adjacent to the hook member, and
an attaching portion defined by the opposite end of the fixing tape substrate, said attaching portion being directly attached to the inner surface of one of said side flaps in a vicinity of an outermost lateral edge of said side flap;
wherein
said fixing tape is folded along the outermost lateral edge of said side flap with said hook member facing said inner surface of said side flap,
the fixing tape substrate has an opening in said attaching portion, a first portion of the inner surface of the respective side flap is exposed though said opening and is directly mechanically, non-adhesively, releasably engaged with said hook member to temporarily fix the folded fixing tape to the inner surface of said side flap, said fixing tape substrate has a second portion being directly contactable with said hook member of the folded fixing tape and having a lower engaging force with said hook member than the first portion.

9. The disposable diaper according to claim 8, wherein the engaging force of said first portion with said hook member is in a range of 0.3 N/25 mm to 2.2 N/25 mm.

10. The disposable diaper according to claim 9, wherein said second portion has an engaging force with said hook member not greater than 2.2 N/25 mm.

* * * * *